(12) United States Patent
Keillor, III

(10) Patent No.: US 6,436,326 B1
(45) Date of Patent: Aug. 20, 2002

(54) FORMING SLURRY OF REACTIVE COMPONENTS AND CONTINUOUSLY FEEDING INTO CONTINUOUS REACTOR

(75) Inventor: Peter T. Keillor, III, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/595,041

(22) Filed: Jun. 15, 2000

Related U.S. Application Data

(60) Provisional application No. 60/139,281, filed on Jun. 15, 1999.

(51) Int. Cl.$^7$ ............... B29C 47/38; C08F 02/01; C08F 02/14; C08L 63/02
(52) U.S. Cl. .............. 264/211.24; 425/381.2; 525/523; 526/64
(58) Field of Search .............. 264/211.24; 526/64; 425/381.2; 525/523

(56) References Cited

U.S. PATENT DOCUMENTS

| | | |
|---|---|---|
| 3,536,680 A | 10/1970 | Illing |
| 3,560,605 A | 2/1971 | Siggel et al. |
| 3,725,340 A | 4/1973 | Erdmenger et al. ..... 264/176 R |
| 3,931,109 A | 1/1976 | Martin .................... 117/128.4 |
| 3,940,453 A | 2/1976 | Labana et al. |
| 4,040,993 A | 8/1977 | Elbling et al. |
| 4,254,071 A | 3/1981 | Flowers et al. ............. 264/102 |
| 4,394,980 A | 7/1983 | März et al. .............. 241/46.02 |
| 4,431,600 A | 2/1984 | Sakamoto et al. ...... 264/176 R |
| 4,448,736 A | 5/1984 | Emery et al. .............. 264/40.1 |
| 4,510,271 A | 4/1985 | Muhle et al. ................ 523/346 |
| 4,569,595 A | 2/1986 | Maillefer ..................... 366/88 |
| 4,612,156 A | 9/1986 | Heinemeyer et al. ... 264/176 R |
| 4,612,355 A | 9/1986 | Belz ............................. 526/65 |
| 4,616,989 A | 10/1986 | Mewes et al. .............. 425/203 |
| 4,708,623 A | 11/1987 | Aoki et al. ................. 425/202 |
| 4,754,413 A | 6/1988 | Köster et al. ............... 364/473 |
| 4,754,645 A | 7/1988 | Piche et al. .................... 73/597 |
| 4,802,769 A | 2/1989 | Tanaka ........................ 366/75 |
| 4,848,915 A | 7/1989 | Fintel ........................... 366/76 |
| 4,870,148 A | 9/1989 | Belz et al. .................... 220/12 |
| 4,909,898 A | 3/1990 | Padliya et al. ............. 159/47.1 |
| 5,075,410 A | 12/1991 | Arpin .......................... 528/96 |
| 5,094,806 A | 3/1992 | Laughner ................... 264/523 |
| 5,165,941 A | 11/1992 | Hawley ...................... 425/148 |
| 5,185,117 A | 2/1993 | Hawley ................. 264/211.12 |
| 5,232,960 A | 8/1993 | Wagner et al. ............. 523/348 |
| 5,310,854 A | 5/1994 | Heinmeyer et al. ......... 528/104 |
| 5,320,753 A | 6/1994 | Keillor, III et al. ......... 210/398 |
| 5,416,148 A | 5/1995 | Farah et al. ................. 524/409 |
| 5,424,367 A | 6/1995 | Auda et al. ................. 525/285 |
| 5,433,112 A | 7/1995 | Piche et al. .................... 73/597 |
| 5,461,089 A | 10/1995 | Handyside et al. ......... 523/171 |
| 5,552,096 A | 9/1996 | Auda et al. .................... 264/85 |
| 5,614,137 A | 3/1997 | Pandit et al. .............. 264/40.6 |
| 5,714,264 A | 2/1998 | Sacharski et al. ........... 428/413 |
| 5,824,752 A | 10/1998 | Beerepoot et al. .......... 525/523 |
| 5,905,111 A | 5/1999 | Leugs et al. ................ 524/560 |

FOREIGN PATENT DOCUMENTS

| | | |
|---|---|---|
| EP | 0 391 372 A3 | 10/1990 |
| GB | 814485 | 6/1959 |
| GB | 1346095 | 2/1974 |
| JP | 61-73743 A   * | 4/1986 |
| JP | HEI 3-26520 | 2/1991 |

OTHER PUBLICATIONS

"Process and Apparatus for Preparing a Composition Using a Continuous Reactor and Mixer in Series", filed in the United States of America on Jun. 15, 2000, application Ser. No. 09/595,040; Applicant: Keillor III, et al.

"Process and Apparatus for Preparing a Composition of Matter Utilizing an Ultrasonic Device", filed in the United States of America on Jun. 15, 2000, application Ser. No. 09/595,042; Applicant: S. J. Maynard.

"Encyclopedia of Polymer Science and Engineering", vol. 12, pp. 1–313.

"Continuous Hydrothermal Synthesis Apparatus", Patent Abstract of Japan, Publication No. 59019540, Kanesaki Taido, Jan. 2, 1984.

"Process and Apparatus for Preparing a Composition of Matter Utilizing a Side Stream Ultrasonic Device", filed in the United States of America on Jun. 15, 2000, application Ser. No. 60/211,736; Applicant: Maynard et al.

Derwent Abstract of EP 0 080 665 B2, Feb., 1983.
Derwent Abstract of EP 309410, Jan. 1989.

* cited by examiner

*Primary Examiner*—Robert E. L. Sellers

(57) ABSTRACT

A process and apparatus for preparing compositions including one or more resinous materials and/or other ingredients using a continuous reactor combined with a slurry vessel for feeding a slurry feed stream to the reactor. More specifically, the process and apparatus prepares a composition by feeding a slurry of one or more reactive monomers and/or oligomers into a continuous reactor extruder to manufacture one or more resinous materials. Optionally, the resinous material may be continuously conveying to a mixer for continuously mixing the resinous material with other ingredients to form a blended composition.

6 Claims, 1 Drawing Sheet

Figure 1:
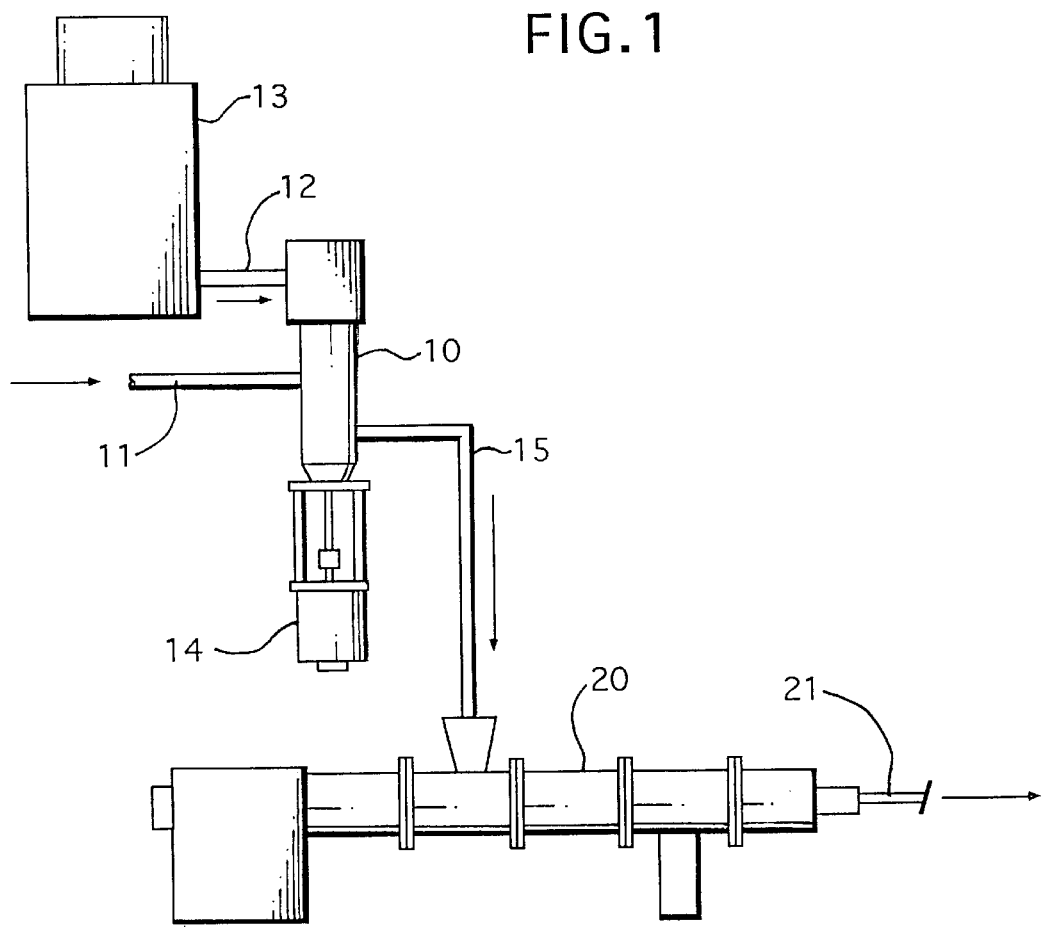

FORMING SLURRY OF REACTIVE COMPONENTS AND CONTINUOUSLY FEEDING INTO CONTINUOUS REACTOR

This application claims the benefit of U.S. Provisional Application No. 60/139,281, filed Jun. 15, 1999.

BACKGROUND OF THE INVENTION

This invention relates to a process and an apparatus for preparing a composition using a continuous extruder. More particularly, this invention relates to a process and an apparatus for preparing a composition by feeding a slurry from a slurry vessel into a continuous reactor.

Heretofore, chemical compositions, for example polymers, have been prepared using continuous reactor extruders. For example, U.S. Pat. No. 4,612,355 discloses the use of extruders for the manufacture of plastics. More specifically, U.S. Pat. No. 4,612,355 discloses the use of reaction extruders to prepare epoxy resins.

Typically, the feed of reactants to such extruders is carried out as solids and or as a melt prior to feeding the extruder. It is difficult to thoroughly and intimately mix the solids together before or while feeding the solids to an extruder. Some chemicals cannot be fed as solids and must be prepared in a different manner.

In addition, feed accuracy demands for continuous processes are high, particularly when the continuous process is plug flow, with minimum backmixing, and a step polymerization. Step polymerizations involving two different di-functional feeds, represented by A—A and B—B, where A reacts with B, are very sensitive to the ratio of A—A and B—B regarding final molecular weight and physical properties.

Generally, liquid feeds are preferred for step polymerization processes, as a feed accuracy of less than 0.1% can be achieved using liquid feeds. However, in some manufacturing processes, one or more of the feeds must be a solid, because a liquid feed form may not be desirable due to degradation or safety concerns. Thus, a solid feed system, such as a loss-in-weight feeder, is required when a liquid feed can not be used. The accuracy of loss-in-weight feeders can approach 0.25% over a one minute interval, but is generally greater than 1% over a 5 second interval. It would be advantageous to avoid having to use a solid feed systems in processes which can not accurately handle solids.

It is therefore desired to provide a process and apparatus for preparing a composition using a slurry feed to a reactor such as an extruder. More preferably, it is desired to provide a process and apparatus which allows averaging of the short term accuracy of a solids feeder by holding up several minutes worth of feed in a continuously stirred, backmixed vessel in combination with a liquid feed.

SUMMARY OF THE INVENTION

The present invention pertains to a process and an apparatus for preparing compositions from one or more resinous materials and other ingredients using a continuous reactor combined with a continuous slurry feed apparatus for feeding the slurry feed stream to the reactor.

In one specific embodiment of the present invention, the present process and apparatus prepares a composition by feeding a slurry of one or more monomers and/or oligomers into a continuous reactor to manufacture one or more resinous materials. The resinous materials may optionally be combined with other additives in a mixer or recovered as a flake for further use.

This process integrates a slurry feeding operation with a reactive extrusion operation. The present invention avoids problems associated with raw materials feed rate variation when using a solid additive to a liquid material without having to melt the solids. The present invention advantageously provides accurate feed flow from a solids feeder.

BRIEF DESCRIPTION OF THE INVENTION

FIG. 1 shows a schematic representation of one embodiment of the apparatus of the present invention and in particular, illustrates a slurry feed vessel in combination with a continuous reactor extruder.

DETAILED DESCRIPTION OF THE PREFERRED EMBODIMENTS

The present invention is directed to a process and an apparatus for achieving consistent feed of a solid feed to a continuous process by using continuously formed and mixed slurry of the solid feed or feeds with a liquid feed. Generally, a loss-in-weight feeder is used to feed the solid to the slurry mixing vessel, and an accurate liquid metering system is used to feed each liquid feed used in the slurry.

The level in the slurry process is controlled by the speed of a pump that forwards the slurry to the process. The level should be measured by a means that does not introduce gas into the system, such as a diaphragm level transmitter or ultrasonic level transmitter. Consistent level control is required to provide a steady feed rate to the process and to ensure adequate mixing. The level in the vessel is controlled at a point above the agitator to create a vortex capable of entraining the solids. The loss in weight feeder discharge should drop the solid feed directly into the vortex.

One embodiment of the present process and apparatus of the present invention involves the preparation of a composition and/or certain resinous materials that are contained within the composition using a reactor extruder in combination with a slurry vessel.

The term "slurry" herein means one or more solid materials suspended in a liquid material.

With reference to FIG. 1, there is shown a slurry vessel 10 connected to a reactor 20. A liquid monomer stream in conduit 11 from storage vessel (not shown) may be heated by an exchanger (not shown) and rate added to the slurry vessel 10 using a rate addition pump (not shown) or alternately a control valve (not shown). The temperature of the liquid monomer stream 11 is controlled to produce a slurry stream that is pumpable. In some cases, the liquid monomer stream 11 is heated to a temperature required to melt any solid monomers present in the slurry vessel 10.

A solid monomer stream in conduit 12 from a solid addition system 13 is rate added to the slurry vessel 10 and a high speed mixer 14 in the slurry vessel 10 combines the solid and liquid monomers to form the reactive slurry stream in conduit 15. The slurry stream 15 is continuously rate added to the reactor 20 using rate addition pump (not shown). If required to complete the reaction, the slurry 15 is combined with a catalyst from catalyst addition pump (not shown). The slurry and catalyst may be combined together in the slurry feed line 15 or alternatively in a high speed inline mixer (not shown) located within slurry line 15 and fed into the continuous reactor 20.

The monomers and other additives such as a catalyst added to the continuous reactor 20 are heated to sufficient temperatures required to produce a reaction within the reactor and ultimately a reaction product stream in conduit 21 exits the reactor 20.

Although not shown, various other embodiments of the present invention, may include for example, where the output of the continuous reactor 20 such as a resinous material is force conveyed through a conduit connecting the continuous reactor 20 with a continuous mixer using a resinous material pump. A liquid additive storage tank and metering flow control pump can also be attached to the system to add any liquid additives or other ingredients to the resinous material before conveying to the mixer. A preferred process and apparatus useful in the present invention for combining a reactor with a mixer is described in copending U.S. patent application, Attorney Docket No. 44646, entitled "Process and Apparatus For Preparing A Composition Using A Continuous Reactor And Mixer In Series" filed by Keillor et al., of even date herewith, incorporated herein by reference.

In addition, the conditions of the resinous material from continuous reactor must be modified before introduction into the continuous mixer. For example, a filter system may be used to remove any particulate matter from the resinous material; or a heat exchanger system may be used to reduce the temperature of the resinous material to the required temperatures for proper mixing. Other solid ingredients may be added from a continuous addition system to the mixer and combined with the resinous material feed stream. At the solids discharge end of the continuous mixer, the product may be transferred to a flaker to solidify and form the product into flakes the composition.

In another variation of the design illustrated in FIG. 1, multiple continuous slurry feed streams may be fed to the continuous reactor or one slurry feed stream may be fed to multiple continuous reactors.

In one embodiment of the present invention, the resinous material, which may be used as a component in the preparation of a composition prepared in the present invention, may be prepared by the process of the present invention in a continuous reactor. The continuous reactor used for this purpose may be a pipe or tubular reactor, or an extruder. It is preferred to use an extruder. More than one such reactor may be used for the preparation of different resinous materials. Any number of reactors may be used and optionally any or all of the reactors may be connected directly to a mixer in which the composition may also be prepared. A pipe or tubular joint is suitable for use as the means of making such connection.

The resinous material useful in the present invention is prepared by polymerizing one or more monomers and/or oligomers in a continuous polymerization reactor to form the resinous material, more specifically a polymer. Typically, a catalyst may be added to the polymerization reaction mixture for the purpose of obtaining a specific type of resinous material, or a desired rate of conversion. The monomer(s), oligomer(s), and catalyst when desired, may, each separately or in groups of two or more, be fed to the polymerization reactor in one or more of the following forms: a liquid solution, a slurry, or a dry physical mixture. However, at least one or more of the components is fed into the reactor extruder as a slurry.

The resinous material from which a composition is prepared according to the present invention may be virtually any polymer or copolymer. The resinous material need not have any particular molecular weight to be useful as a component in the composition. The resinous material may have repeating units ranging from at least two repeating units up to those resinous materials whose size is measured in the hundreds or thousands of repeating units. Particular resinous materials that may be used in the methods of the present invention include for example, epoxy resins, polyesters, urethanes, acrylics and others as set forth in U.S. Pat. No. 5,094,806, which is incorporated herein by reference. The most preferred resinous materials useful in the present invention from among those listed above are epoxy resins and polyesters. Epoxy resins useful in the present invention, and materials from which epoxy resins may be prepared, are described in U.S. Pat. No. 4,612,156, which is incorporated herein by reference. Polyesters useful in the present invention, and materials from which polyesters may be prepared, are described in Volume 12 of *Encyclopedia of Polymer Science and Engineering*, pages 1–313, which pages are incorporated herein by reference.

In the production of a resinous material to be used as a component of a composition of the present invention, various conditions or parameters have an effect on the course of the polymerization reaction. Typical examples of these conditions or parameters are as follows: the rate of feed to the reactor of the monomer(s) and/or oligomer(s); the temperature at which the reaction occurs; the length of time during which the reaction occurs; and the degree to which the reactants are mixed or agitated during the reaction. The rate of feed of monomer(s) and/or oligomer(s) can be influenced, for example, by valve adjustment on a pressured line. The temperature at which the reaction occurs can be influenced, for example, by the direct heating or cooling of the monomer(s) and/or oligomer(s) or to the reactor itself. The length of time during which the reaction occurs can be influenced, for example, by the size of the reactor, such as the length of a pipe, tube or extruder, or the speed at which the reactants move into and out of the reactor, such as may result from the particular speed or design of an extruder screw, or the introduction of a pressurized inert gas into a pipe or tube. The degree to which the reactants are mixed or agitated during the reaction can be influenced, for example, by the size, shape and speed of blades or other mixing elements, by the presence of a static mixing element in a pipe or tube, or the speed of the screw in an extruder.

The quality of the composition prepared by the process and apparatus of the present invention is improved if the properties of the resinous material to be used as a component in the composition are known and maintained at a desired level. Typical examples of resinous material properties that may be analyzed for this purpose are viscosity, melt index, melt flow rate, molecular weight, molecular weight distribution, equivalent weight, melting point, glass transition temperature, density, specific gravity, and purity. For example, when an epoxy resin is used as a resinous material, it is desired that its viscosity be in the range of from about 1 to about 100,000 centipoise. The analytical techniques that may be used to determine resinous material properties such as the foregoing include ultrasonic wave energy, Raman, infrared, near infrared, and dielectrics energy. A preferred process and apparatus for measuring properties of the resinous material used in the present invention is described in copending U.S. patent application Ser. No. 09/595,042, entitled "Process And Apparatus For Preparing A Composition of Matter Utilizing An Ultrasonic Device", filed by Shawn Maynard, of even date herewith incorporated herein by reference.

Generally, the compositions prepared by the slurry process of the present invention are prepared by continuously feeding a reactive slurry solution from a slurry vessel to a reactor extruder. Any number of other ingredients may be added to the slurry vessel, to the line feed of the reactor or to the reactor to form a composition. For example, one or more polymers that have not been prepared in a reactor, reactive or inert compounds, or additives such as pigments, filler or stabilizer. Optionally, when the final composition is a blend of materials, the composition from the reactor extruder may be conveyed from the reactor to a mixer through a connection between the reactor and the mixer to form a composition. If more than one reactor is used, a connection is established between each reactor and the mixer.

The preferred type of mixer to use is an extruder, particularly a twin-screw extruder but other types of mixers such as co-kneaders may be used as well.

In another embodiment of the present invention, a composition may be prepared by compounding the resinous material with other components to prepare a final composition. The remaining components of the final composition includes a number of other ingredients which may also include a resinous material, such as an epoxy or a polyester, or other resinous materials listed above. The remaining components of the composition may also include ingredients such as conventional additives for example hardeners for an epoxy resin (e.g. dicyandiamide), fillers, pigments and stabilizers. Other additives as ingredients for the composition prepared by the process and apparatus of the present invention are disclosed in U.S. Pat. No. 5,416,148, which is incorporated herein by reference. Such additives may be incorporated as a liquid into the composition. After mixing the composition in the mixer, the composition is recovered in a form suitable for handling, such as in the form of a flake or pellet.

EXAMPLE 1

Solid epoxy resins were prepared via the reaction of a liquid epoxy resin and bisphenol A. The feeding of molten bisphenol A to a reactor extruder was deemed unacceptable for this application due to color buildup upon shutdown and startup. Thus, liquid epoxy resin and bisphenol A were fed to a slurry vessel in a continuous manner at desired flow rates as shown in Table 1 below. Slurry from the slurry vessel was then continuously fed to a Krupp Werner & Pfleiderer ZSK-40 reactor extruder using a Moyno™ progressing cavity pump and "The Probe" ultrasonic level measurement. The epoxide equivalent weight of the product produced in the reactor was measured over time as indicated in Table 1I. Consistency of the EEW was acceptable, demonstrating the efficacy of the slurry feed system. The following table shows the results of this Example.

TABLE 1

| SAMPLE # | TIME | LER RATE (lb/hr) | BISPHENOL RATE (lb/hr) | EEW |
|---|---|---|---|---|
| #1 | 1545 | 101.716 | 38.284 | 688.5 |
| #2 | 1600 | 101.716 | 38.284 | 675.1 |
| #3 | 1615 | 101.716 | 38.284 | 678.8 |
| #4 | 1630 | 101.716 | 38.284 | 685.2 |
| #5 | 1645 | 101.716 | 38.284 | 680.8 |
| #6 | 1700 | 101.716 | 38.284 | 691.2 |
| #7 | 1715 | 101.716 | 38.284 | 683.2 |
| #8 | 1730 | 101.716 | 38.284 | 690.3 |

What is claimed is:

1. A process for preparing a composition of matter comprising the steps of:

(a) continuously preparing a slurry of reactive components selected from the group consisting of resinous materials, monomers, oligomers and mixtures of monomers and oligomers of the composition of matter in a stirred slurry vessel, the slurry containing at least one solids component and at least one liquid component;

(b) continuously feeding the slurry of components of the composition of matter from the slurry vessel into at least one continuous reactor, such that a consistent feed of a solids feed is achieved;

(c) continuously forming the composition of matter in the reactor from said slurry, and (d) recovering said composition of matter from said reactor.

2. The process of claim 1 wherein the composition of matter is a resinous material.

3. The process of claim 2 wherein the resinous material is a polymer.

4. The process of claim 1 wherein the slurry comprises monomers or mixtures of monomers and oligomers.

5. The process for claim 3 wherein the polymer is an epoxy resin.

6. The process of claim 1 wherein the reactor is an extruder.

* * * * *